United States Patent [19]

Dellinger

[11] 4,360,341

[45] Nov. 23, 1982

[54] ORTHODONTIC METHOD FOR TREATING MALOCCLUSION

[76] Inventor: Eugene L. Dellinger, 1326 Old Lantern Trail, Fort Wayne, Ind. 46825

[21] Appl. No.: 243,873

[22] Filed: Mar. 16, 1981

[51] Int. Cl.³ .............................................. A61C 3/00
[52] U.S. Cl. .......................................... 433/24; 433/3
[58] Field of Search ................................. 433/24, 3, 9

[56] References Cited

U.S. PATENT DOCUMENTS

| | | | |
|---|---|---|---|
| 3,345,745 | 10/1967 | Muller | 433/9 |
| 3,521,355 | 7/1970 | Pearlman | 433/3 |
| 3,686,762 | 8/1972 | Sutter | 433/3 |
| 3,738,005 | 6/1973 | Cohen et al. | 433/24 |
| 3,787,976 | 1/1974 | Cohen | 433/3 |
| 3,871,098 | 3/1975 | Dean | 433/3 |
| 3,949,477 | 4/1976 | Cohen et al. | 433/24 |
| 3,949,478 | 4/1976 | Schinhammer | 433/24 |
| 4,014,096 | 3/1977 | Dellinger | 433/24 |
| 4,160,322 | 7/1979 | Frazier | 433/24 |
| 4,284,405 | 8/1981 | Dellinger | 433/24 |

Primary Examiner—Gene Mancene
Assistant Examiner—John J. Wilson
Attorney, Agent, or Firm—Gust, Irish, Jeffers & Hoffman

[57] ABSTRACT

The invention comprehends the use of a fixture which fits over a tooth on which a bracket is to be affixed, this fixture having an internal cavity which essentially matches the shape and contour of a portion of the tooth, such as the lingual surface and incisal edge, the remaining portion of the fixture extending downwardly in spaced juxtaposition with respect to the labial surface. This labial space is slightly greater than the height of a standard bracket. The juxtaposed surface of the fixture is preferably provided with a smoothly contoured irregularity adapted to mate with a plastic or the like bracket-orienting module having a complementary surface portion, the opposite portion of this module being contoured to nest in or over the labial portion of a bracket. This contoured module portion may include a projection which slidably fits the bracket slot. Thus, with a bracket fitted onto the projection with the module in place in the fixture, the bracket is positively oriented in a precise location relative to the fixture.

By forming the module-orienting portion of the fixture in registry with the desired location of the bracket on the tooth, the fixture and the orienting module can be used to position precisely a bracket on the patient's tooth.

9 Claims, 11 Drawing Figures

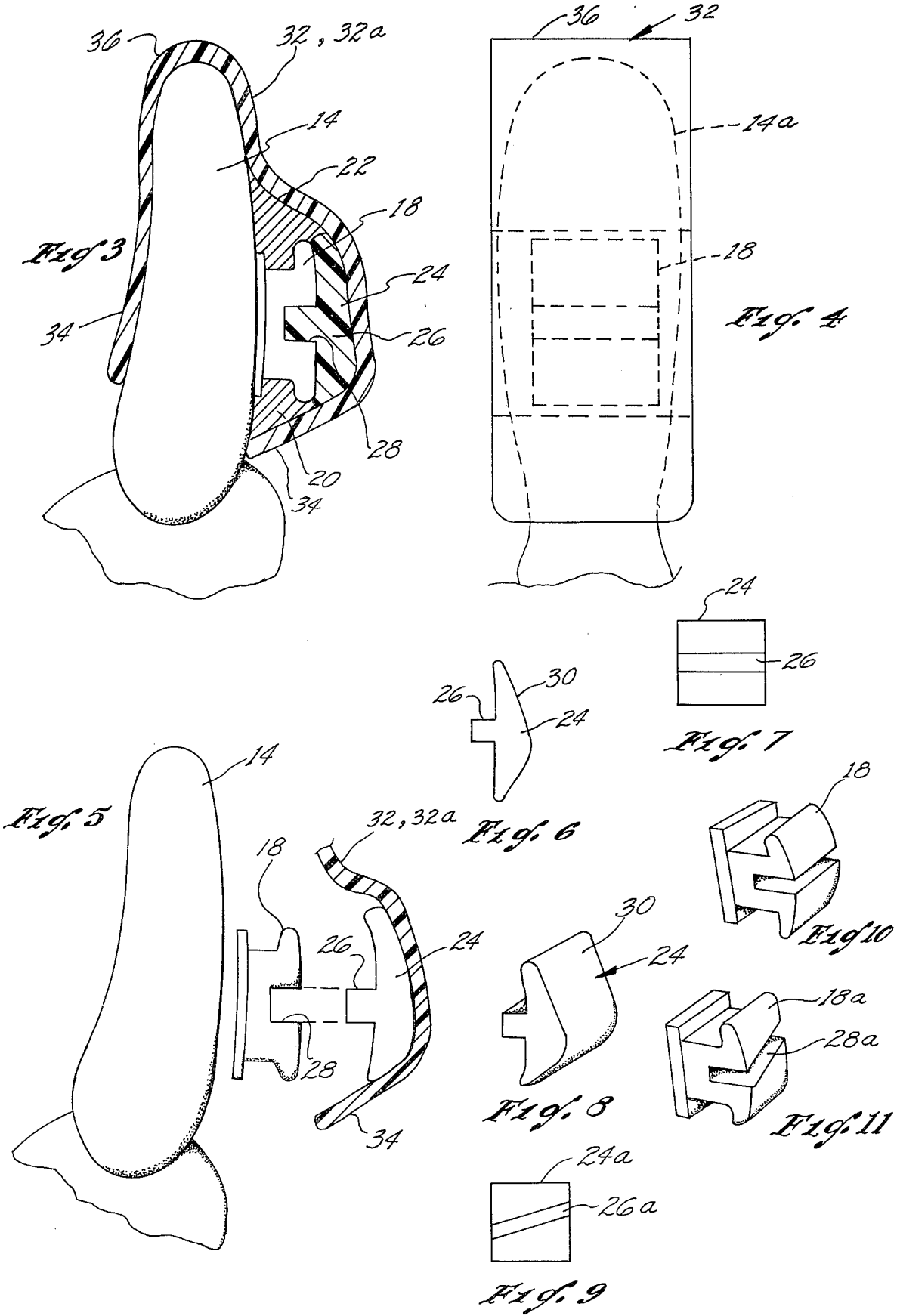

ORTHODONTIC METHOD FOR TREATING MALOCCLUSION

BACKGROUND OF THE INVENTION

1. Field of the Invention

The present invention relates to orthodontics and more particularly to a method and apparatus useful in precisely locating a bracket on a patient's tooth.

2. Description of the Prior Art

Prior art methods and apparatuses for precisely locating brackets on patient's teeth are disclosed in U.S. Pat. Nos. 4,014,096; 4,160,322; 4,183,141 and 3,738,005. Of importance in following such procedures is the precise and correct placement of brackets upon the teeth utilizing in some instances idealized laboratory models to predetermine such placement. In certain of the aforesaid patents, brackets are mounted on the model in positions which conform to an idealized coplanar archwire shape, while in others, prefabricated brackets are ideally located on the model and eventually incorporated into a transfer mask conforming to the malocclusion for placement on the pateint's teeth to initiate treatment. In still other of such patents, bracket-holding devices are incorporated into transfer masks adapted to be registered over patient's teeth. The bracket-holding devices or portions thereof serve in locating the brackets on the teeth in positions corresponding to those selected on the model.

SUMMARY OF THE INVENTION

The present invention relates to an apparatus and method by means of which brackets may be easily and precisely located on and affixed to a patient's teeth in accordance with a fixed standard. The standard may be customized as to a particular patient or established by one of a series of typical case setups.

This invention finds particular utility in a technique in which the slots of the brackets on the patient's teeth positionally correspond to that predetermined on an idealized laboratory model to be coplanar. When treatment of the patient is completed, the bracket slots are coplanar according to the slot arrangement on the idealized model. While a coplanar geometry is preferred, it may include buccal-lingual steps or deviations from a common plane. In order to accomplish this treatment, it is necessary that the brackets be precisely located on the patient's teeth, and it is to this requirement that the present invention is particularly directed.

In one method of this invention, the bracket is positioned in a precise location on a patient's tooth as predetermined according to the steps of forming a locating fixture with an internal cavity provided with lingual and labial sides having one portion complementary to preselected surface anatomy of a given tooth and a second portion spaced from the labial surface of the same tooth, fitting a bracket-orienting element onto the second portion in a predetermined relationship therewith as determined by mating, orienting portions on both the element and the second portion, the element having a bracket-receiving portion adapted to orient a bracket relative to the second portion, engaging a bracket with the bracket-receiving portion, and transferring the bracket to the patient's tooth by registering said one portion of the cavity of the fixture with the preselected tooth surface anatomy.

It is an object of this invention to provide a method and apparatus which facilitates treatment of malocclusion.

It is another object of this invention to provide a method and apparatus for positioning brackets onto teeth with a high degree of precision.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

In the drawings.

FIG. 3 is an enlarged sectional view taken substantially along section line 3—3 of FIG. 2;

FIG. 4 is a labial view of the tooth arrangement of FIG. 3;

FIG. 5 is an exploded view used in explaining the steps and the method of this invention;

FIG. 6 is an end view of one of the bracket-orienting designs;

FIG. 7 is a rear view thereof;

FIG. 8 is a perspective view;

FIG. 9 is a rear view of another module design; and

FIGS. 10 and 11 are perspectives of typical brackets.

DESCRIPTION OF THE PREFERRED EMBODIMENT

Figure 1:
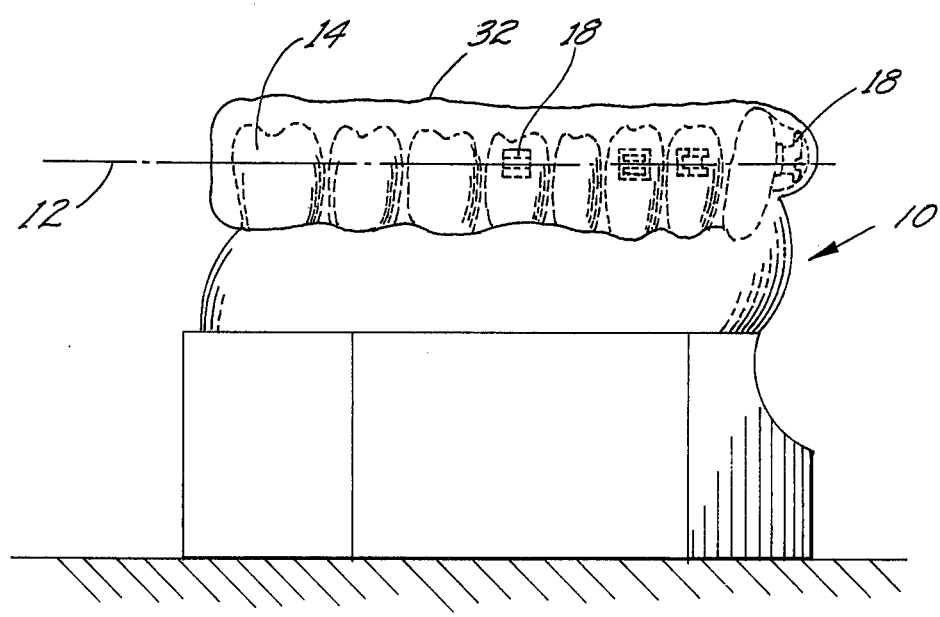
FIG. 1 is a side elevation of an idealized model of a dental arch illustrating one portion of the method of this invention.
Figure 2:
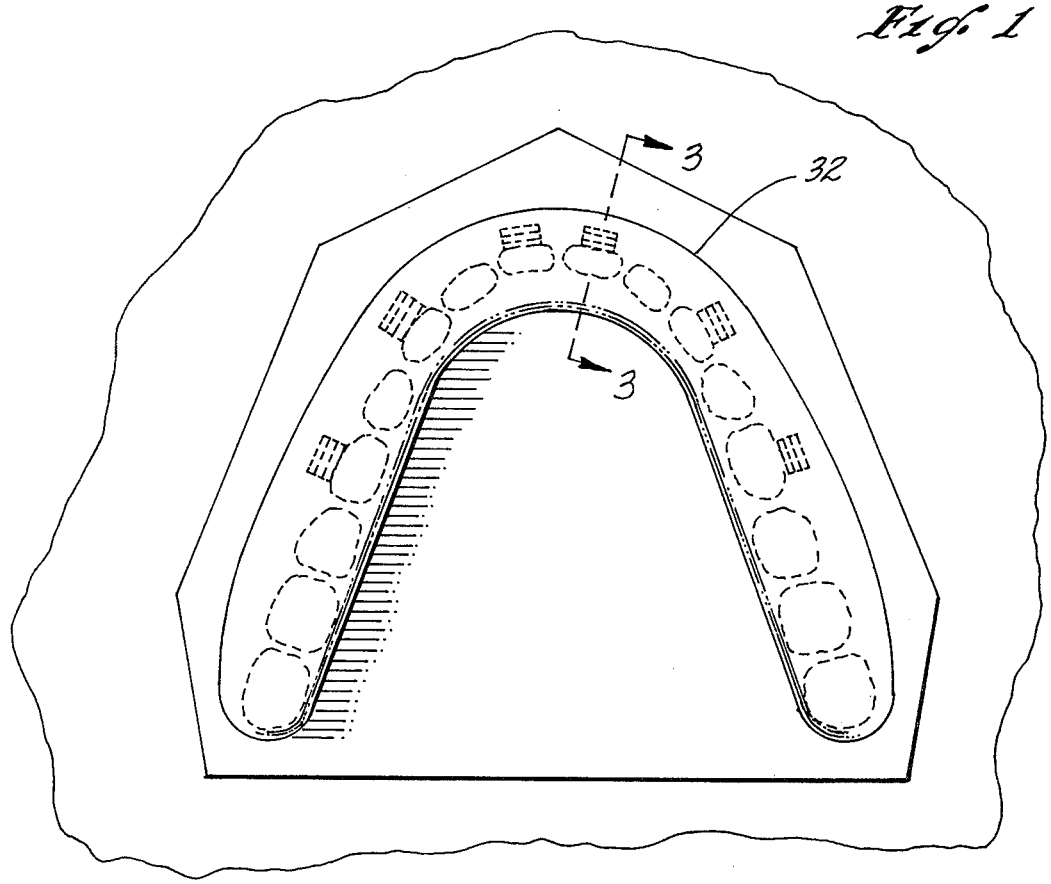
FIG. 2 is a top plan view thereof.

In practicing the present invention, an idealized model of the patient's teeth is produced in accordance with conventional practice and otherwise as disclosed in Dellinger U.S. Pat. No. 4,014,096. A coplanar line or mark 12 is drawn on the tooth replicas 14. The position of the line 12 on each replica 14 is selected by the clinician to coincide with the desired location of the slot in a bracket to be directly bonded to the replica. The line 12 around the entire dental arch will correspond to the shape of an arch wire, preferably smoothly curvilinear and coplanar, to be used in the final stages of treatment. Other line patterns may be used without departing from the spirit and scope of this invention.

Suitable brackets 18 are bonded to the replicas 14 with the slots in registry with the line 12. A suitable filler material such as wax or a hardenable putty is filled into the shape surrounding the bracket and in engagement with the labial surface of the replica 14. This filler, indicated by the numeral 20 has its outer surface 22 smoothly contoured as shown for a purpose which will become apparent from the description that follows.

Next performed, bracket-orienting modules 24 are assembled to the labial portions of the respective brackets 18 there being one module for each bracket. As shown more clearly in FIGS. 6 through 8, the width and length of the module coincides with the corresponding dimensions of the labial portion of the bracket 18, the projection 26 thereof being sized to slidably fit into the bracket slot 28. Thus assembled, the module and bracket are positionally interlocked against movement except for separation. The outer surface 30 of the module 24 is angularly contoured to be asymetrical as viewed in FIG. 6 but otherwise is smoothly rounded at the corners. As shown in FIG. 3, the filler 20 is contoured such that the outer surface 22 smoothly merges with the module surface 30. The module 24 thus has opposed inner and outer locating portions 26, 30.

With the assembled brackets, modules and filler portions on the respective replicas, a plastic cap or fixture 32 having the shape of the dental arch is formed over the replicas 14 to extend to the gingiva in intimate engagement with the incisal edges, lingual surfaces of the replicas and the surfaces 22 and 30 as clearly shown in FIG. 3. The fixture thus has lingual surface and incisal edge portions conforming to the surface anatomy of the corresponding portions of a patient's tooth. The labial side of the fixture extends generally parallel to the labial side of such tooth but is spaced outwardly therefrom (FIG. 3). The material of the fixture preferably is plastic in liquid, semiliquid or moldable form. The fixture may also be made by vacuum forming a heat moldable material over the replicas and bracket-module assemblies. Once hardened, the fixture is separated from the model, leaving the module 24 and bracket 18 assembled to the replica 14. The fixture upon being removed from the model will have to be formed so as to pass over the module 24, therefore the wall thickness and plastic material used should have a corresponding degree of resilience.

In the embodiment as shown in FIG. 3, the fixture is extended downwardly as indicated by the numeral 34 to just engage the labial surface of the tooth at a point slightly below the gum line. In using the fixture on a patient, the gum line may be slightly depressed by this extension 34 to facilitate the bonding of a bracket. This would find its maximum utilization for bonding brackets to posterior teeth.

Preferably, the arch shaped fixture 32 as shown in FIG. 1 is now sectioned into units, one for each replica. FIGS. 3 and 4 are illustrative. The fixture unit 32a may now be used to transfer a bracket, line bracket 18, to the corresponding tooth 14a (FIG. 4) in the patient's mouth. This may be accomplished by removing the bracket 18 from the replica as indicated in FIG. 5. The module 24 is registered with or disposed within the mating portion or cavity of the fixture (FIG. 5) and the bracket 18 is assembled to the module 24. This positions bracket 18 for placement on the labial side of the patient's tooth to which it is to be fitted. The fixture is then fitted over the corresponding tooth 14a of the patient with the lingual and incisal cavity portions fitting precisely, or in other words conforming to the surface anatomy of, the corresponding shape and irregularities of the lingual and incisal portions of the tooth. The labial side of the fixture unit extends generally parallel to the labial side of the tooth but is spaced outwardly therefrom (see FIG. 3). The module is thus disposed within the cavity in juxtaposed relation with the labial surface of such tooth. Since the bracket 18 is positively oriented with respect to the fixture unit 32a, the bracket 18 will be positioned on the patient's tooth in precisely the same position as it was on the replica.

Bonding of the bracket to the tooth is accomplished by applying cement to the tooth or bracket base before the fixture unit is applied to the tooth. The fixture unit is held in position until the cement cures. It is then removed along with the module 24. Brackets are applied to the other teeth in a patient's mouth in the same way. Once installed, a smoothly curvilinear archwire conforming to the shape and size of the bracket slots on the idealized model is secured in the bracket slots in accordance with conventional practice. Assuming that none of the brackets become damaged or lost during the treatment period, once the teeth have been moved to positions at which the slots and the brackets are coplanar and otherwise conform to the shape of the coplanar archwire, the treatment is essentially complete.

If during treatment a particular bracket becomes dislodged or broken, it may be replaced by an identical bracket in precisely the same position by using the same fixture and module combination. Thus the replacement fits into the pattern of treatment the same as the original.

Brackets having different slot configurations may be similarly precisely positioned on the patient's teeth by using the same fixture units 32a. As shown in FIGS. 10 and 11, the two brackets are of essentially the same size and shape except that the bracket 18a of FIG. 11 has its slot 28a set at an angle. This requires the use of a different orienting module such as 24a of FIG. 9 which is identical in every respect to the module 24 with the exception that the projection 26a is formed at an angle corresponding to that of slot 28a. With this module and bracket assembled and the module then mated with the fixture unit 32a, the bracket 18a may be positioned on the patient's tooth in the same position as the bracket 18.

By the same token, brackets of different width using the same modules 24 and 24a may also be precisely positioned.

Standard brackets of common manufacture may be of common size and shape with only the slot being varied. Thus, the module 24 instead of having a slot-receiving projection like projections 26 and 26a can be provided with a shallow socket or recess (not shown) which complements the head or labial portion of the bracket, the projection 26 and 26a being omitted. The edges of the socket are smoothly rounded and overlie the edges of the bracket head only minimally and just enough to orient positively the bracket with respect to the module. Using this modified design thus dispenses with requiring an inventory of modules having different projections 26, 26a, the same module being useful with brackets having different slot angles and locations.

Thus, it becomes apparent that the same fixture unit 32a may be used repeatedly for mounting different brackets, one requirement being that the orienting module be configured to mate properly with the labial portion of the bracket to be bonded to the tooth. The clinician may, therefore, maintain an inventory of different bracket-module combinations, the feature in common being the contour of the outer surface portion of the module mating with the orienting surface on the fixture unit.

Duplicates of the fixture units may be made and kept by the clinician for subsequent use should the initial fixture become lost or damaged. Duplicates of the modules may also be inventoried.

The fixtures may be fabricated from an ideal or overcorrected setup for a particular patient or may be selected from various prefabricated standards which conform to the more common setups. Such fixtures fabricated from models of some of the more common case setups may be given tooth and size designations by means of which the clinician could select the most appropriate fixture-module combination for a given case to be treated. So long as the same combination is used, a bracket can be placed upon the tooth in a precise position as predetermined by the fixture-module used.

By utilizing the method and apparatus of this invention, brackets may be direct bonded to the teeth in a patient's mouth in precise and correct positions which will enable finishing treatment by means of a pre-configured archwire and which may be coplanar without buccal-lingual steps. The archwire may be other than coplanar and provided with such steps as may be predetermined by the clinician, the modules and the fixtures having been fabricated according to the predetermined archwire shape. During treatment, should any bracket become dislodged or damaged, it can be replaced in precisely the same position as the original by utilizing the bracket orienting fixtures and modules disclosed. Since the bracket-locating fixtures and modules are prefabricated, free hand placement and many of the judgment factors involved on the part of the practitioner are eliminated.

While there have been described above the principles of this invention in connection with specific apparatus, it is to be clearly understood that this description is made only by way of example and not as a limitation to the scope of the invention.

What is claimed is:

1. The method of positioning a bracket in a predetermined position on a patient's tooth comprising the steps of forming a locating fixture with an internal cavity provided with lingual and labial or buccal sides having one portion complementary to preselected surface anatomy of a given tooth and a second portion spaced from and overlying in general parallelism one of the labial, buccal or lingual surfaces of said tooth, fitting a bracket-orienting element onto said second portion in a predetermined relationship therewith as determined by mating orienting portions on both said element and said second portion, said element having a bracket-receiving portion adapted to orient a bracket relative to said second portion, engaging a bracket with said bracket-receiving portion, said element thereby being disposed within said cavity, and transferring said bracket to the patient's tooth by registering said one portion of the cavity of said fixture with said preselected tooth surface anatomy.

2. The method of claim 1 including the steps of contouring the mating portions to provide complementary surfaces, and forming said bracket-receiving portion into a projection shaped and sized to have a sliding fit with the slot of a bracket.

3. The method of claim 2 including the further step of forming said bracket-receiving portion with a surface which complements the face of said bracket on opposite sides of the slot thereof.

4. The method of claim 3 wherein preselected surface anatomy includes the lingual side and incisal edge of said given tooth.

5. The method of fabricating an orthodontic appliance and repositioning a patient's teeth, comprising the steps of:

forming a model of the patient's teeth in the shape of a dental arch with the replicas of the teeth ideally located, mounting brackets on selected replicas in preselected locations, fitting bracket-orienting modules to the labial or buccal portions of said brackets, respectively, forming a fixture of hardenable plastic material over the crowns of said selected replicas and over said modules in intimate conformity with the respective incisal edges, lingual surfaces and said modules, and utilizing the replica portions of said fixture and one or more of said modules to locate brackets on the corresponding teeth in the patient's mouth.

6. The method of claim 5 including the step of dividing said fixture into units, one for each replica, and fitting said units with the respective modules therein over the corresponding teeth in the patient's mouth for locating the brackets thereon.

7. The method of claim 6 including the step of forming each module with a projection having a sliding fit with the slot in a bracket, said projection fitting the slot in the bracket on the replica as well as in the bracket located on the patient's tooth.

8. The method of claim 5 including the steps of forming the outer surfaces of said modules with smooth surfaces having mold relief contours, the plastic of said fixture, when hardened, being resiliently flexible, and removing said fixture and modules from said replicas and brackets, dividing said fixture into units, one for each replica, and said utilizing step including fitting the same or a different bracket onto the projection of a module and the module into the conforming cavity in the fixture unit, and placing the assembled fixture unit over a corresponding tooth in the patient's mouth thereby locating the bracket on such tooth.

9. The method of claim 5 wherein the brackets on the replicas have undercut portions between the heads and bases thereof, filling said undercuts with a filler material to provide a smoothly contoured surface extending from the faces of the brackets outwardly therefrom and angled toward said replicas, respectively, then forming said fixture as aforesaid over the replicas, modules and filler, whereby the resulting cavity in said fixture formed by the respective module and cavity will have a mold relief contour to facilitate removal of said fixture from said mold.

* * * * *